(12) United States Patent
Mansfield et al.

(10) Patent No.: US 7,052,874 B2
(45) Date of Patent: May 30, 2006

(54) **DETECTION OF ANTIBACTERIAL ACTIVITY IN EXCRETORY SECRETORY PRODUCT OF ADULT *TRICHURIS SUIS***

(75) Inventors: Linda S. Mansfield, Bath, MI (US); Sheila R. Abner, Atlanta, GA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 172 days.

(21) Appl. No.: 10/415,166

(22) PCT Filed: Nov. 6, 2001

(86) PCT No.: PCT/US01/44070

§ 371 (c)(1),
(2), (4) Date: Apr. 25, 2003

(87) PCT Pub. No.: WO02/062836

PCT Pub. Date: Aug. 15, 2002

(65) Prior Publication Data

US 2004/0029802 A1    Feb. 12, 2004

Related U.S. Application Data

(60) Provisional application No. 60/246,203, filed on Nov. 6, 2000.

(51) Int. Cl.
*C12P 1/00* (2006.01)
*C12P 21/00* (2006.01)

(52) U.S. Cl. .................. 435/71.3; 41/70.1; 41/71.1
(58) Field of Classification Search ............ 435/71.1, 435/70.1, 41, 71.3
See application file for complete search history.

(56) References Cited

OTHER PUBLICATIONS

Abner et al. Abstracts of the General Meeting of the American Society for Microbiology. vol. 99, 1999, p. 221.*
Rhoads et al. Experimental Parasitology. Jan. 2000, vol. 94, No. 1, pp. 1-7.*
Kato et al. Journal of Enzyme Inhibition. 1994, vol. 8, No. 1, pp. 25-37.*
Wardlaw et al. Journal of Applied Bacteriology. 1994. vol. 76, pp. 36-41.*

* cited by examiner

*Primary Examiner*—Vera Afremova
(74) *Attorney, Agent, or Firm*—Ian C. McLeod

(57) ABSTRACT

The present invention provides a heat-stable and protease-resistant antibacterial activity in excretory-secretory products (ESP) of *Trichuris suis*. The antibacterial activity is not more than 10,000 MW; is resistant to boiling, trypsin, and pronase E; has a bactericidal mode of action; and is effective against Gram positive and Gram negative bacteria, including *Escherichia coli, Campylobacter jejuni, Campylobacter coli*, and *Staphylococcus aureus*. The antibacterial activity is useful in applications for killing or inhibiting the growth of microorganisms, in particular bacteria.

8 Claims, 6 Drawing Sheets

DETECTION OF ANTIBACTERIAL ACTIVITY IN EXCRETORY SECRETORY PRODUCT OF ADULT *TRICHURIS SUIS*

CROSS-REFERENCE TO RELATED APPLICATION

This application claims priority to Provisional Application No. 60/246,203, which was filed Nov. 6, 2000.

Reference to a "Computer Listing Appendix submitted on a Compact Disc"
Not Applicable.

STATEMENT REGARDING FEDERALLY SPONSORED RESEARCH OR DEVELOPMENT

This invention was supported by National Institutes of Health Grant No. AI42348-03. The U.S. government has certain rights in this invention.

BACKGROUND OF THE INVENTION (1) Field of the Invention

The present invention relates to heat-stable and protease-resistant antibacterial activity in excretory-secretory products (ESP) of *Trichuris suis*. The antibacterial activity is not more than 10,000 MW; is resistant to boiling, trypsin, and pronase E; has a bactericidal mode of action; and is effective against Gram positive and Gram negative bacteria, including *Escherichia coli, Campylobacter jejuni, Campylobacter coli*, and *Staphylococcus aureus*. The antibacterial activity is useful in applications for killing or inhibiting the growth of microorganisms, in particular bacteria.

(2) Description of Related Art

Compounds with antibacterial activity have been identified from a wide array of invertebrates, including parasitic nematodes (Wardlaw et al., J. Appl. Bacteriol. 76: 36–41 (1994); Kato, Zoo. Sci. 12: 225–30 (1995)). These factors constitute a primitive humoral defense system. It is not surprising that metazoan parasites inhabiting the gastrointestinal tract (GI) produce antibacterial substances, since they are in a microbe-rich environment containing potential pathogens. For example, a potent antibacterial activity was found in the body fluid of *Ascaris suum*, a nematode parasitizing the pig small intestine (Wardlaw et al., J. Appl. Bacteriol. 76: 36–41 (1994); Kato, Zoo. Sci. 12: 225–30 (1995)). The bactericidal activity was heat stable and less than 14,000 MW in size. Subsequently, three humoral defense activities (antibacterial, bacteriolytic, and agglutinating) were detected in the body fluid of *A. suum* (Kato, Zoo. Sci. 12: 225–30 (1995)).

The *A. suum* antibacterial factor (referred to as ASABF) has been well-characterized (Kato and Komatsu, J. Biol. Chem. 271: 30493–30498 (1996)). ASABF is a heat-stable and trypsin-sensitive peptide of 71 amino acids (Kato and Komatsu, J. Biol. Chem. 271: 30493–30498 (1996)). ASABF has structural and functional similarities to the defensins of insects/arthropods. Both are cysteine-rich, cationic peptides that are more effective against Gram positive bacteria than Gram negative bacteria (Kato and Komatsu, J. Biol. Chem. 271: 30493–30498 (1996)). ASABF has significant sequence identity with the proteins deduced from a cDNA sequence (yk150c7) and from a putative gene (T22H6.5) of *Caenorhabditis elegans*, a free-living nematode (Kato and Komatsu, J. Biol. Chem. 271: 30493–30498 (1996)).

A gene family of saposin-like proteins has been identified in *C. elegans*, with one of them (T07C4.4) having antibacterial activity when expressed as a recombinant in *E. coli* (Banyai and Patthy, Biochim. Biophys. Acta 1429: 259–64 (1998)). The putative products of these *C. elegans* genes are similar to the amoebapores of *Entamoeba histolytica* and a putative amoebapore-related protein of the liver fluke *Fasciola hepatica* in that they consist of a single saposin-like domain and a secretory signal peptide (Banyai and Patthy, Biochim. Biophys. Acta 1429: 259–64 (1998)). Amoebapores of *E. histolytica*, an invasive protozoan pathogen, are pore-forming peptides with antibacterial an cytolytic activities, which function by formation of ion channels in target cell membranes (Andra, et al., FEBS Letters 385: 96–100 (1996); Leippe et al., Molec. Microbiol. 14: 895–904 (1994)).

Antibacterial activity in invertebrates is quite common. Antibacterial peptides have been described from the silkworm, *Bombyx mori* (Chowdhury, et al., Biochem. Biophys. Res. Comm. 214: 271–8 (1995); Hara and Yamakawa, J. Biol. Chem. 270: 29923–7, (1995); Kim et al., Biochem. Biophys. Res. Comm. 246: 388–92 (1998)). A proline-rich antibacterial peptide from the earthworm, *Lumbricus rubellus*, has been reported (Cho et al., Biochim. Biophys. Acta 1408: 67–76 (1998)). Antibacterial agents have also been detected in two other annelid species, *Nereis diversicolor* (Salzet-Raveillon et al., Cell. Molec. Biol. 39: 105–14 (1993)) and *Eisenia foetida* (Kauschke and Mohrig, Devel. Compar. Immunol. 11: 331–41 (1987)).

Most of the antimicrobial agents identified from invertebrates are peptides that exhibit structural similarities. Insect defensins are cationic, cysteine-rich peptides forming intramolecular disulfide bridges that appear in the hemolymph after bacterial challenge or injury (Cociancich et al., J. Biol. Chem. 268: 19239–45 (1993)). They have potent antibacterial activity against Gram positive bacteria mediated by disruption of the permeability barrier of the cytoplasmic membrane (Cociancich et al., J. Biol. Chem. 268: 19239–45 (1993)). The myticins found in the haemocytes of the mussel, *Mytilus galloprovincialis*, are cysteine-rich and exemplify antibacterial peptides originating as precursors with signal sequences that require proteolytic events to activate the mature peptide (Mitta et al., Eur. J. Biochem. 265: 71–8 (1999)). Antibacterial peptides offer a means for treating or preventing bacterial infections that is not based upon an antibiotic mode of activity.

Antibiotics are commonly used to prevent bacterial infections. However, because many antibiotics have been used with relative abandon over the past half century, many microorganisms have developed resistance to many of the antibiotics. As a consequence, many antibiotics have been rendered ineffective at preventing bacterial infections. Unless new antibiotics or alternative antibacterial treatments are developed, the world will be staring at a public health crisis of immense proportions. Therefore, there is a dire need for novel antibacterial compositions for preventing bacterial infections.

SUMMARY OF THE INVENTION

The present invention provides at least one heat-stable and protease-resistant antibacterial activity in excretory-secretory products (ESP) of *Trichuris suis*. The antibacterial activity is not more than 10,000 MW, has a bactericidal mode of action, and is effective against Gram positive and Gram negative bacteria, including *Escherichia coli, Campylobacter jejuni, Campylobacter coli*, and *Staphylococcus*

*aureus*. The antibacterial activity is useful in applications for killing or inhibiting the growth of microorganisms, in particular bacteria.

Therefore, the present invention provides an excretory-secretory product of *Trichuris suis* comprising at least one antibacterial activity which inhibits the growth of *Campylobacter jejuni* as an assay strain in a growth medium and wherein the antibacterial activity is resistant to boiling, freeze-thawing, trypsin, and pronase E.

The present invention further provides a method for producing an excretory-secretory product with at least one antibacterial activity which inhibits the growth of *Campylobacter jejuni* as an assay strain in a growth medium and which is resistant to boiling, freeze-thawing, and proteases which comprises (a) culturing *Trichuris suis* in vitro in a serum-free medium; and (b) separating the excretory-secretory product with the antibacterial activity from the medium.

Further still, the present invention provides a method for inhibiting a microorganism which comprises contacting the microorganism with an excretory-secretory product of *Trichuris suis* which comprises at least one antibacterial activity which inhibits the growth of *Campylobacter jejuni* as an assay strain in a growth medium and which is resistant to boiling, freeze-thawing, trypsin, and pronase E in an amount which inhibits the microorganism. In a particular embodiment of the method, the microorganism is a bacterium.

Further still, the present invention provides a composition comprising at least one antibacterial activity isolated from excretory-secretory products of *Trichuris suis* which inhibits the growth of *Campylobacter jejuni* as an assay strain in a growth medium and wherein the antibacterial activity is resistant to boiling, freeze-thawing, trypsin, and pronase E in a carrier. Preferably, the carrier is selected from the group consisting of filler, non-toxic buffer, physiological saline solution, water, alcohol, ointment, cream, gel, balm, paste, liquor, tincture, elixir, tablet, lotion, paste, capsule, spirit, and perenteral solution.

The present invention further provides a method for isolating an isolated antibacterial activity from excretory-secretory products of *Trichuris suis*, wherein the antibacterial activity inhibits the growth of *Campylobacter jejuni* as an assay strain in a growth medium and wherein the antibacterial activity is resistant to boiling, freeze-thawing, trypsin, and pronase E, comprising (a) culturing the *Trichuris suis* in vitro in a serum-free medium to produce the excretory-secretory products; (b) removing the antibacterial activity from components of the secretory-excretory products which are greater than 10,000 MW; (c) separating the antibacterial activity removed from the secretory products which are greater than 10,000 MW by column chromatography; and (d) eluting the antibacterial activity from the column to produce the isolated antibacterial activity wherein the antibacterial activity inhibits the growth of *Campylobacter jejuni* as an assay strain in a growth medium and wherein the antibacterial activity is resistant to boiling, freeze-thawing, trypsin, and pronase E. Preferably, the column chromatography is HPLC and wherein the HPLC uses a reverse phase C18 column and a gradient to separate the antibacterial activity, preferably, wherein the gradient is a 5–80% acetonitrile gradient in 0.1% trifluoroacetic acid. Preferably, the antibacterial activity is eluted from the HPLC column at between about 1 to 10 minutes, at between about 40 to 50 minutes, or at between about 60 to 70 minutes.

In any one of the above embodiments of the present invention, the antibacterial activity has a minimum inhibitory concentration and a minimum bactericide concentration of the bacterial activity which are about the same.

Further still in any one of the above embodiments of the present invention, the excretory-secretory product of the *Trichuris suis* has an antibacterial activity which is not more than 10K MW.

Further still in any one of the above embodiments, the antibacterial activity inhibits at least 50% of at least one species of Gram positive or Gram negative bacteria. In particular, the above embodiment wherein the antibacterial activity inhibits a bacteria selected from the group consisting of *Campylobacter jejuni*, *Campylobacter coli*, *Escherichia coli*, and *Staphylococcus aureus*.

OBJECTS

It is an object of the present invention to provide an antibacterial activity from the excretory-secretory products of *Trichuris suis* for use in antibacterial applications.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The initial observation that the excretory-secretory products (ESP) from *Trichuris suis*, a parasitic nematode found in the large intestine of pigs, contained novel antibacterial activity was in a tissue culture invasion assay against *Campylobacter jejuni*. Herein, is disclosed the novel antibacterial activity of the present invention isolatable from the ESP collected from *Trichuris suis* adults cultured in vitro.

The term "trichuricin" refers to the novel antibacterial activity isolatable from the ESP of *Trichuria suis*. As shown herein, trichuricin comprises at least three novel antibacterial activities as determined by HPLC of a 10K filtrate of the ESP on a reverse phase C18 column developed with a 5–80% ACN gradient in 0.1% TFA. The novel antibacterial activities may be related or distinct. As used herein, trichuricin refers to any one of the novel antibacterial activities and to any combination of the three novel antibacterial activities.

The term "antimicrobial activity" refers to the ability of the trichuricin of the present invention to inhibit or kill at least one species selected from the group consisting of Gram positive bacteria, Gram negative bacteria, fungi, and protozoans. In general, it is increasingly preferred that the trichuricin inhibits or kills at least 50%, 60%, 70%, 80%, 90% or all cells of at least one species of Gram positive or Gram negative bacteria, fungi, or protozoans. Sensitive bacteria include, but are not limited to, *Campylobacter jejuni*, *Campylobacter coli*, *Escherichia coli*, and *Staphylococcus aureus*.

Figure 5A:
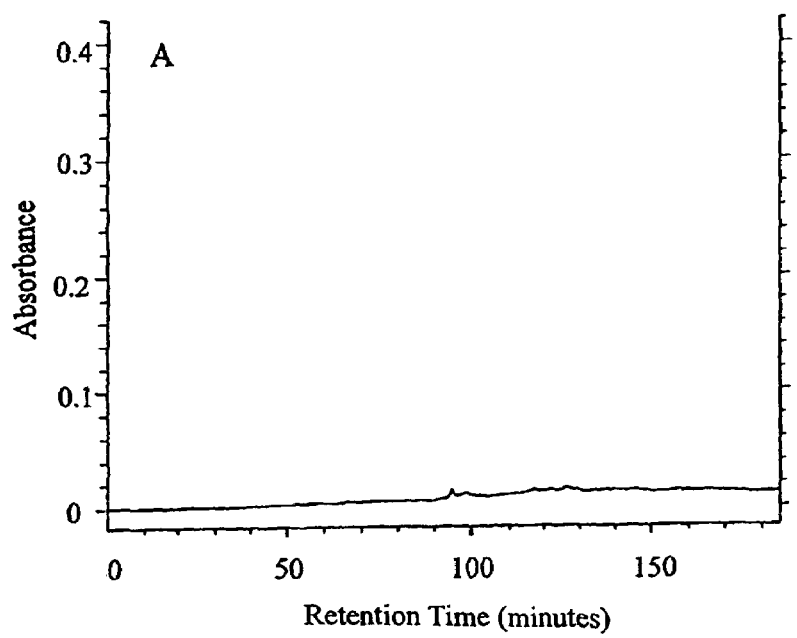
FIG. 5A shows that the CAP-free ESP 10K retentate fractionated on a reverse-phase C18 HPLC column with a 5–80% ACN gradient in 0.01% TFA had no antibacterial activity. Sample was 10 µg in 0.02 ml and antibacterial activity was determined by the qualitative broth microdilution assay.
Figure 5B:
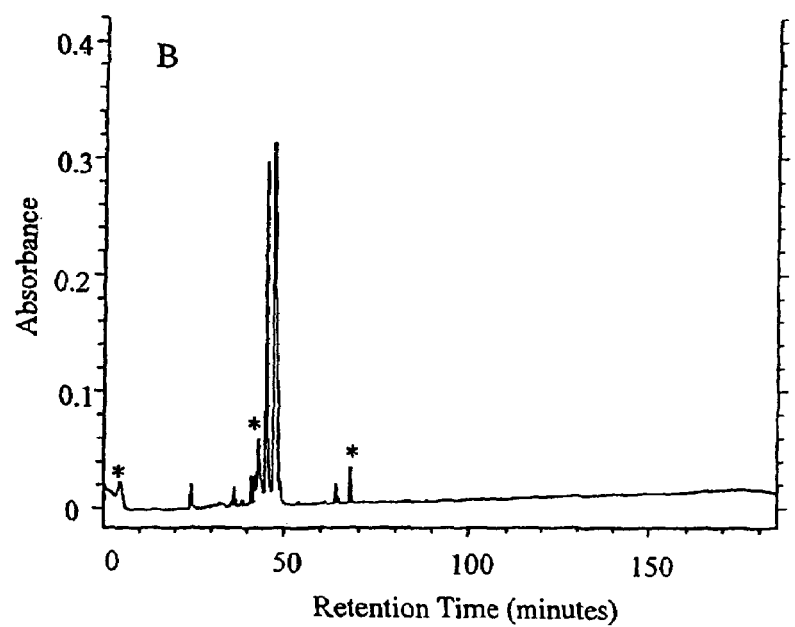
FIG. 5B shows that the CAP-free ESP 10K filtrate fractionated on a reverse-phase C18 HPLC column with a 5–80% ACN gradient in 0.01% TFA had two fractions with antibacterial activity. Sample was 10 μg in 0.02 ml and antibacterial activity was determined by the qualitative broth microdilution assay.

The trichuricin of the present invention is separable from ESP by HPLC into at least three fractions, each with antibacterial activity as determined by broth microdilution assays using *Campylobacter jejuni* 33292 as the assay strain. The antibacterial activity of the trichuricin comprises at least three peptides, each of which has antibacterial activity, and each of which are heat stable and resistant to digestion with pronase E and trypsin. The trichuricin peptides each have a molecular weight of not more than about 10,000 Daltons as determined by filtering the ESP through a filter with a 10K MW cut-off and fractionating the filtrate by HPLC. Trichuricin has the HPLC profile shown in FIG. 5B wherein a 0.2 ml volume of the 10K filtrate of the ESP is loaded onto a reverse phase C18 column and developed with a 5–80% ACN gradient in 0.1% TFA. As shown in FIG. 5B, the trichuricin antibacterial activities are eluted from the HPLC column at between about 1 to 10 minutes for antibacterial activity 1, between about 40 to 50 minutes for antibacterial activity 2, and between about 60 to 70 minutes for antibacterial activity 3 as shown in FIG. 5B. Trichuricin is expected to have a bactericidal mode of action because the minimum inhibitory concentration (MIC) and the minimum bactericidal concentration (MBC) of its antibacterial activity are about the same.

The specific activity of trichuricin varies from preparation to preparation because of the inherent variability attendant in preparing ESP starting with infected pigs. However, in general, the unpurified ESP has about 2,560 activity units (AU)/ml or 853 AU/mg protein (as determined by the inhibitory effect of the ESP on the *Campylobacter jejuni* 33292 test strain in broth microdilution assays as shown in Tables 1 and 7). Further, as shown in Table 7, the 10K filter purified trichuricin exhibited about 10,240 AU/ml or about 102,400 AU/mg protein (using *Campylobacter jejuni* 33292 as the test strain). The AU/ml is the reciprocal of the greatest serial dilution of ESP or filtrate that inhibits the *Campylobacter jejuni* 33292. For example, a 50 μl aliquot of the 10K filtrate was serial diluted and the antibacterial activity of each dilution was determined. Because the 10K filtrate had 10,240 AU/ml, a 50 μl aliquot of the 10K filtrate for serial dilution contained 512 AU which was the reciprocal of the greatest serial dilution that still had antibacterial activity. Therefore, the minimum antibacterial concentration (MIC) of the antibacterial activity in the 10K filtrate is 1 AU of a 10,240 AU/ml 10K filtrate preparation or about 10 ng of protein. In contrast, the MIC of the antibacterial activity in the ESP was 1 AU of a 2,560 AU/ml ESP preparation or about 1.2 μg of protein. In light of the above, the minimum antibacterial activity of the trichuricin is 1 AU using *Campylobacter jejuni* 33292 as the standard.

The novel antibacterial activity of the trichuricin, which is at least active at a neutral pH and at 37° C., inhibits the growth of both Gram positive and Gram negative bacteria. In particular, the novel antibacterial activity inhibits the growth of *Campylobacter jejuni*, *Campylobacter coli*, *Escherichia coli*, and *Staphylococcus aureus*.

The trichuricin of the present invention enables the treatment or control of microbial infections caused by those organisms which are sensitive to trichuricin. Such treatment or control includes administering to a host or tissue susceptible to or afflicted with a microbial infection an antimicrobially effective amount of the trichuricin. Preferably, the trichuricin includes all three antibacterial activities when used to treat or control microbial infections.

A antimicrobially effective amount of the trichuricin can be readily determined according to methods known in the art. For agricultural use, the composition comprises an antimicrobially effective amount of the trichuricin and an agriculturally acceptable carrier suitable for the organism (e.g., plant) to be treated. For example, for use in a pharmaceutical composition, the trichuricin can have an $ED_{50}$ in vitro less than about $10^{-3}$ M. One with ordinary skill in the art can readily determine an antimicrobially effective amount of the trichuricin against a target bacterial strain, for example, based on the $ED_{50}$ using the methods disclosed herein and the teachings of the art.

Because of the antibacterial properties of the trichuricin, it can also be used as a preservative or a sterilant of materials susceptible to microbial contamination. For example, an antimicrobially effective amount the trichuricin of the present invention can be used as a disinfectant for treating surfaces and can be incorporated into compositions such as foods, cosmetics, animal feeds, and the like to impart an antibacterial activity to the composition which prevents spoilage of the composition.

Furthermore, pharmaceutical compositions comprising the trichuricin of the present invention as an active ingredient in an antimicrobially effective amount to produce the antibacterial effect in a susceptible host or tissue and a pharmaceutically acceptable, non-toxic sterile carrier can be readily prepared based on the teachings provided herein and in the art. Such carriers can be fillers, non-toxic buffers, physiological saline solution, and the like, including, but not limited to, water, alcohol, solvents and oils in the form of aromatic waters, liquors, solutions, ointment, cream, gel, balm, paste, tinctures, elixirs, spirits, and perenteral solutions. The preparation can be used topically or systemically and may be in any suitable form such as liquid, solid or semi-solid, which includes injectable solutions, tablets, ointments, lotions, pastes, capsules and the like. For example, the trichuricin can be incorporated into an ointment and used as a topical antibacterial application to the skin, a cut, a scratch, or wound to prevent or treat an infection. In addition, the trichuricin can also be administered in combination with other adjuvants or compatible drugs where such a combination is seen to be desirable or advantageous in controlling an infection caused by harmful microorganisms.

Compositions comprising the antimicrobially effective amount of trichuricin can be given via a route of administration suited to the form of the composition. Such compositions are, for example, in the form of usual liquid preparations including solutions, suspensions, emulsions and the like which can be given orally, as a dental rinse, gingivally, topically, intravenously, subcutaneously, or intramuscularly. The composition is administered in an antibacterially effective amount, generally a dose of about 0.01 to about 100 mg/kg/day, calculated as protein is expected to be useful. However, the optimum upper and lower therapeutic amounts and any contra-indications have not yet been fully established.

Antibiotics are commonly used to prevent bacterial infections. However, many microorganisms have developed resistance to many of the antibiotics. As a consequence, many antibiotics are no longer effective at preventing bacterial infections. While new antibiotics may be developed which will prevent bacterial infections, it would be more desirable to develop bactericides which in general are more difficult for bacteria to develop resistance to. Because the trichuricin of the present invention is bactericidal in nature, trichuricin is an improvement over antibiotics as a means for preventing bacterial infections.

To prepare trichuricin from pig intestines, pigs are infected with about 2500 viable *Trichuris suis* eggs by oral gavage. After about 45 to 50 days, the pigs are killed 45 to 50 days after infection. The entire GI tract is removed from the pig and the GI tract slit open longitudinally, the contents emptied into a bucket, and adult whipworms picked individually from the colon with forceps into successive petri dishes of sterile saline pre-warmed to 37° C. The intestinal contents are washed through a 2 mm sieve with tap water and additional whipworms are recovered from the sieve. All damaged or immature whipworms are eliminated and any remaining debris adhering to the whipworms is removed.

After washing the whipworms in sterile saline, the whipworms are washed in sterile media such as Hanks balanced salt solution (HBSS) to remove fine debris not visible under the microscope. This is followed by incubation in a 5×-concentrated antibiotic cocktail containing 500 U/ml penicillin (PEN), 500 µg/ml streptomycin (STREP) and 1.25 µg/ml amphotericin B (AMB) in a medium such as RPMI-1640 for a 16 to 24 hr period. A second incubation in a 1× antibiotic cocktail containing PEN, STREP, and AMB is performed for an additional 16 to 24 hr period. The whipworms are then washed repeatedly in sterile media, at least 3 changes for a minimum of 2 hr each, to remove residual antibiotics. Finally, the whipworms are incubated for 10 days in a media such as RPMI-1640 containing 1% glucose (about 4 whipworms/ml) at 37° C. with humidified 5% $CO_2$ for production of whipworm-conditioned media containing ESP.

To confirm sterility of the whipworm-conditioned media containing ESP, aliquots are plated on blood agar plates and incubated aerobically and anaerobically at 37° C. for at 48 hrs or more. Contaminated batches are discarded. Whipworm-conditioned media containing the ESP are collected daily, pooled, and filtered through a 10,000 MW cutoff filter to produce a solution containing the trichuricin free of higher molecular weight material. The filtrate is sterile filtered and stored at −80° C. until use.

The trichuricin is further purified from the filtrate by HPLC. The filtrate is loaded onto a reverse phase C18 column preferably packed with a Vydak 300 angstrom resin and developed with a 5–80% acetonitrile (ACN) gradient in 0.1% trifluoroacetic acid (TFA). The trichuricin antibacterial activity is eluted from the HPLC column as a first antibacterial activity at between about 1 to 10 minutes, as a second antibacterial activity at between about 40 to 50 minutes, and as a third antibacterial activity at between about 60 to 70 minutes. The eluted trichuricin fractions are pooled, sterile filtered, and stored at −80° C. until use. Alternatively, each trichuricin elution fraction is separately sterile filtered and stored at −80° C. until use.

As is readily apparent, it would be desirable to be able to produce the trichuricin without relying on infected pigs. Therefore, the trichuricin is preferably produced by a recombinant organism containing DNA encoding the trichuricin. The recombinant organism includes, but is not limited to, a yeast wherein the DNA encoding the trichuricin is integrated into the yeast genome, a transgenic plant wherein the DNA encoding the trichuricin is integrated into the plant genome, a mammalian cell wherein the DNA encoding the trichuricin is in an expression vector such as the Simliki forest virus expression vector, an insect cell wherein the DNA encoding the trichuricin is in a baculovirus expression vector, and a bacterium which is not susceptible to the trichuricin or a bacterium wherein the promoter for expressing the DNA encoding the trichuricin is an inducible promoter such as the lacZ promoter.

The following examples are intended to promote a further understanding of the present invention.

EXAMPLE 1

This example illustrates the discovery and subsequent isolation of the novel trichuricin from the ESP of *Trichuris suis* and further provides a preliminary analysis of the novel trichuricin.

MATERIALS AND METHODS

Experimental infection of pigs and recovery of adult *Trichuris suis*. Weaned pigs, were maintained in confinement housing and provided pig chow and water ad libitum. The pigs were experimentally infected with approximately 2500 viable *Trichuris suis* eggs by oral gavage. Pigs were killed 45 to 50 days after infection with a captive bolt gun. The necropsy procedure involved opening the abdomen and removing the entire GI tract. The GI tract was slit open longitudinally, contents emptied into a bucket, and adult whipworms plucked from the colon with forceps. Intestinal contents were washed through a 2 mm sieve with tap water and additional whipworms were recovered from the sieve. Whipworms were picked individually using forceps into successive petri dishes of sterile saline pre-warmed to 37° C. When all damaged or immature whipworms were eliminated and whipworms appeared clean visually, they were examined under a dissecting scope and any remaining debris adhering to the whipworms was removed.

Preparation of Trichuris suis ESP. The Trichuris suis ESP used in the original experiments was prepared from adult whipworms pulled free from the colonic mucosa as described above and in Hill et al. (Exper. Para. 77: 170–8 (1993)). After washing in sterile saline, the whipworms were washed in sterile Hanks balanced salt solution (HBSS) to remove fine debris not visible under the microscope. This was followed by incubation in a 5×-concentrated antibiotic cocktail in RPMI-1640 for a 16 to 24 hr period. The original 5× cocktail contained 500 U/ml penicillin (PEN), 500 μg/ml streptomycin. (STREP), 1.25 μg/ml amphotericin B (AMB), and 350 μg/ml chloramphenicol (CAP). A second incubation in a 1× antibiotic cocktail without CAP was performed for an additional 16–24 hr period. The whipworms were then washed repeatedly in sterile HBSS, at least 3 changes for a minimum of 2 hr each, to remove residual antibiotics. Finally, the whipworms were incubated for 10 days in RPMI-1640 containing 1% glucose (4 whipworms/ml) at 37° C. with humidified 5% $CO_2$ for collection of whipworm-conditioned media containing ESP. To confirm sterility, aliquots of ESP were plated on blood agar plates and incubated aerobically and anaerobically at 37° C. for at least 48 hrs. Contaminated batches were discarded. ESP was collected daily, pooled, and concentrated at 4° C. by ultrafiltration using an AMICON stir cell (Millipore, Bedford, Mass.) with a 10,000 MW cutoff to 1/20th of the original volume. The total protein content of 20×-concentrated ESP was determined using the Bradford assay, which ranged from 3–4 mg protein/ml. Concentrated ESP was sterile filtered (0.22 μm; Millipore, Bedford, Mass.) and stored at −80° C. As a control for the volume reduction step, RPMI-1640 media containing 1% glucose without whipworms was concentrated under the same conditions. Bovine serum albumin (BSA) added to concentrated RPMI (cRPMI) was also used as a control for protein content.

Bacterial strains and media. The antibacterial activity in Trichuris suis ESP was originally observed using Campylobacter jejuni (ATCC 33292), and this was the strain on which most experiments were performed for this preliminary characterization. Several Campylobacter jejuni and Campylobacter coli isolates were used for MIC determinations (Table 1).

TABLE 1

MICs of Trichuris suis ESP on Campylobacter spp.

| Campylobacter jejuni | | Campylobacter coli | |
|---|---|---|---|
| Strain | MIC | Strain | MIC |
| 33292[a] | 1:128 | 1679368 | 1:32 |
| 33560 | 1:128 | 17010887 | 1:64 |
| 43430 | 1:256 | 18439 | 1:64 |
| 43470 | 1:128 | 1935 | 1:64 |
| 19084571 | 1:64 | 1777708 | 1:64 |
| 15046764 | 1:512 | 17140 | 1:128 |
| 19094451 | 1:256 | 43473 | 1:64 |
| 43433 | 1:64 | 43474 | 1:64 |
| 33291 | 1:128 | 43479 | 1:32 |

TABLE 1-continued

MICs of Trichuris suis ESP on Campylobacter spp.

| Campylobacter jejuni | | Campylobacter coli | |
|---|---|---|---|
| Strain | MIC | Strain | MIC |
| 43429 | 1:128 | 43482 | 1:64 |
| 49349 | 1:256 | 43134 | 1:64 |

Suspensions of Campylobacter jejuni (about $5 \times 10^5$ cfu) were added to serial two-fold dilutions of 20×-concentrated ESP. The MIC was the highest dilution with no growth after 48 hours incubation.
[a]Campylobacter jejuni strain 33292 was used in subsequent experiments as the test organism for characterization of the antibacterial activity in Trichuris suis ESP.

Additional quality control organisms routinely used for antimicrobial susceptibility assays were tested, including Enterococcus faecalis (ATCC 29212), Staphylococcus aureus (ATCC 25923), Escherichia coli (ATCC 25922), Pseudomonas aeruginosa (ATCC 27853), and Streptococcus pneumonia (ATCC 49619). Campylobacter jejuni and Campylobacter coli were grown on Mueller-Hinton agar supplemented with 5% sheep blood or in Mueller-Hinton broth (MHB) in humidified 5% $CO_2$ to achieve a microaerophilic atmosphere. S. pneumoniae was grown aerobically on blood agar plates; all other strains were grown on tryptic soy agar plates under aerobic conditions. All organisms were incubated at 37° C.

Antibacterial activity assays. Agar diffusion and broth microdilution methods were used to characterize the antibacterial activity of Trichuris suis ESP (NCCLS. Methods for Dilution Antimicrobial Susceptibility Tests For Bacteria That Grow Aerobically. Fourth Ed. (1997)). For the agar diffusion assay, susceptibility discs were saturated with 20 μl ESP samples at various concentrations and applied to plates inoculated confluently with the test organism. Plates were observed for zones of growth inhibition surrounding each disc after incubation for 24 hr for all organisms except Campylobacter spp., for which results were recorded after 48 hr. For the susceptible control organisms listed previously, the effect of the inoculum concentration was assessed. For this experiment, suspensions of the organisms at $10^8$ cfu/ml were serially diluted to achieve $10^7$, $10^6$, and $10^5$ cfu/ml suspensions for inoculation of agar plates.

A broth microdilution method in 96 well plates was used to obtain qualitative and quantitative measures of antibacterial activity. Qualitatively, 50 μl samples of ESP were added to 50 μl suspensions of Campylobacter jejuni (containing about $5 \times 10^5$ cfu, as determined by standard serial dilution and plating) in 96 well plates. Plates were evaluated for growth as indicated by the presence of either turbidity or pellet of bacterial cells in the bottoms of U-shaped wells after 48 hr incubation.

To quantify activity and determine the minimum inhibitory concentration (MIC) of ESP against test organisms, serial two-fold dilutions of 20×-concentrated ESP were prepared in 50 μl volumes of MHB (n=2). Each well was then inoculated with 50 μl of Campylobacter jejuni suspended in MHB at a starting inoculum of about $5 \times 10^5$ cfu, prepared from an overnight (20–24 hr) plate culture of actively motile, early 10 phase organisms. The MIC was assessed as the highest dilution of ESP that resulted in no visible turbidity after 48 hr of incubation. The antibacterial titer was defined as the reciprocal of the MIC and was expressed in activity units (AU) per ml for selected experiments. For each well showing diminished or no turbidity, a 50 µl aliquot was subcultured onto a Mueller-Hinton blood plate and incubated for 48 hr. The minimum bactericidal concentration (MBC) corresponded to the highest dilution that showed no growth upon subculturing.

Stability. Unfractionated ESP was subjected to various treatments and then bioassayed for antibacterial activity using the broth micro dilution assay to evaluate the stability the antibacterial activity. Physical treatments included boiling for 15 minutes and freezing-thawing (3 cycles at −70° C.). Digestions with trypsin and pronase E (Sigma, St. Louis, Mo.) were performed with 1 mg/ml final enzyme concentration on 100 AU/ml ESP at 37° C. for 6 hr. In this experiment, BSA (1 mg/ml) was digested as a control and run on a standard 15% SDS-PAGE gel to confirm that the enzymes were functional under these conditions. Prior to the bioassay, enzymes were inactivated by boiling for 15 minutes. Control experiments were carried out without ESP to confirm that the heat-inactivated trypsin and pronase E were not inhibitory to growth of the test bacteria.

Ultrafiltration. Ultrafiltration methods were used to nominally size fractionate ESP for an approximate determination of the molecular weight of the antibacterial agent(s). AMICON stirred cells under pressurized nitrogen gas were used to separate ESP into fractions above (retentate) and below (filtrate) 30,000 MW with a Millipore YM30 membrane (Millipore) and fractions above (retentate) and below (filtrate) 10,000 MW with a Millipore YM10 membrane. Prior to bioassay, the concentrated retentate fraction was returned to its original volume in RPMI-1640 media to match the volume of the filtrate so that comparisons of relative activity could be made without distortions due to volume differences. Antibacterial activity was assayed in the retentate and filtrate fractions using the agar diffusion method as described above.

High performance liquid chromatography. A Model 173 high performance liquid chromatography (HPLC) system (Perkin Elmer Applied Biosystems, Inc., Foster City, Calif.) at the Michigan State University Macromolecular Structure Facility was used to fractionate *Trichuris suis* ESP for preliminary isolation of the antibacterial activity (Hearn, Meth. Enzymol. 104: 190–212 (1984)). Samples (150 µl) of ESP were mixed with an equal volume of 0.1% trifluoroacetic acid (TFA) and centrifuged at full speed (11,000×g) at room temperature for 15 minutes. Two hundred microliters of the clarified supernatant containing either about 100 µg or 10 µg total ESP protein was injected onto a C18 reverse phase column (0.8 mm in diameter and 250 mm long) packed with Vydak 300 Å resin (LC Packings, San Francisco, Calif.). Compounds were eluted by a continuous linear gradient of 5% acetonitrile (ACN) in 0.1% TFA to 80% ACN in 0.1% TFA over a three-hour period at a flow rate of 0.04 ml/min. Absorbance of the eluate was monitored at 214 nm, and fractions were collected manually as peaks were detected. Eluted fractions were dried in a SAVANT SPEEDVAC concentrator (Savant Instruments, Inc., Hullwood, N.Y.), reconstituted in 50 µl sterile ultrapure water, and filter sterilized (COSTAR SPIN-X columns, Corning Life Sciences, Corning, N.Y.) prior to bioassay for antibacterial activity by the broth microdilution assay.

To address the concern that one or more of the antibiotics used during the whipworm culture procedure could persist if to the final ESP preparation, control HPLC experiments with antibiotic standards were performed for comparison to ESP chromatograms. Initially, 1× concentrations of PEN (100 U/µl), STREP (100 µg/ml), AMB (0.25 µg/ml), and CAP (70 µg/ml) were performed for screening purposes. A subsequent experiment with CAP at 2 µg/ml was then carried out.

Mass spectrometry. Fast atom bombardment-mass spectrometry (MS) was used as an assay for residual antibiotics in ESP potentially carried over in the solution or adherent to the whipworms during preparation (Burlingame et al., Anal. Chem. 70: 647R–716R (1998)). Mass spectra were obtained using a JEOL HX-110 double-focusing mass spectrometer (JEOL USA, Peabody, Mass.) operating in the positive ion mode. Ions were produced by bombardment of samples in a glycerol matrix with a beam of Xe atoms (6 keV) or $Cs^+$ ions (12 keV). The accelerating voltage was 10 kV and the resolution was set at 1000. The instrument was scanned in 30 seconds from m/z 50 to 1000.

Consideration of CAP contamination. After detection of residual CAP in the original ESP, multiple measures were taken to exclude the possibility that the antibacterial activity of the ESP was an artifact of CAP contamination. Using the worst-case scenario, the predicted maximum amount of CAP absorbed and how much would be released into the medium if the whipworms dissolved (i.e., released 100%) was estimated. However, it was more likely that very little of the drug was released back into the medium due to the equilibrium (plateau) established during uptake. For estimating the predicted amount, the log PC value (n-octanol/water partition coefficient) was used, which is a measure of lipophilicity, and anthelminthic drug absorption kinetic data in model nematodes, *Ascaris suum* and *Haemonchus contortus* (Ho et al., Mol. Biochem. Para. 41: 153–65 (1990); Ho et al., Mol. Biochem. Para. 52: 1–13 (1992); Ho et al., J. Pharma. Sci. 83: 1052–9 (1994)). It was assumed that the aggregate whipworm volume of these eccentrically shaped nematodes occupied 4% of the incubation well volume (4 whipworms/ml at about 10 µl/whipworm).

PEN and STREP were also included in this assessment, although AMB was excluded because it is an antifungal agent, which does not inhibit the growth of *Campylobacter jejuni* or the other test bacteria used in these studies. The size of the drug was also taken into consideration. Additionally, an experiment to assess the heat stability of the antibiotics was performed.

The definitive test was to prepare ESP in the complete absence of CAP for subsequent control experiments that would parallel selected experiments performed with the original ESP. For these experiments, a local farm with naturally *Trichuris suis*-infected pigs was identified as a source of whipworms to prepare the CAP-free ESP. The same protocol was used except that CAP was omitted from the 5× antibiotic cocktail treatment. Also, the 10K filtrate was saved for experimentation.

RESULTS

Figure 1:
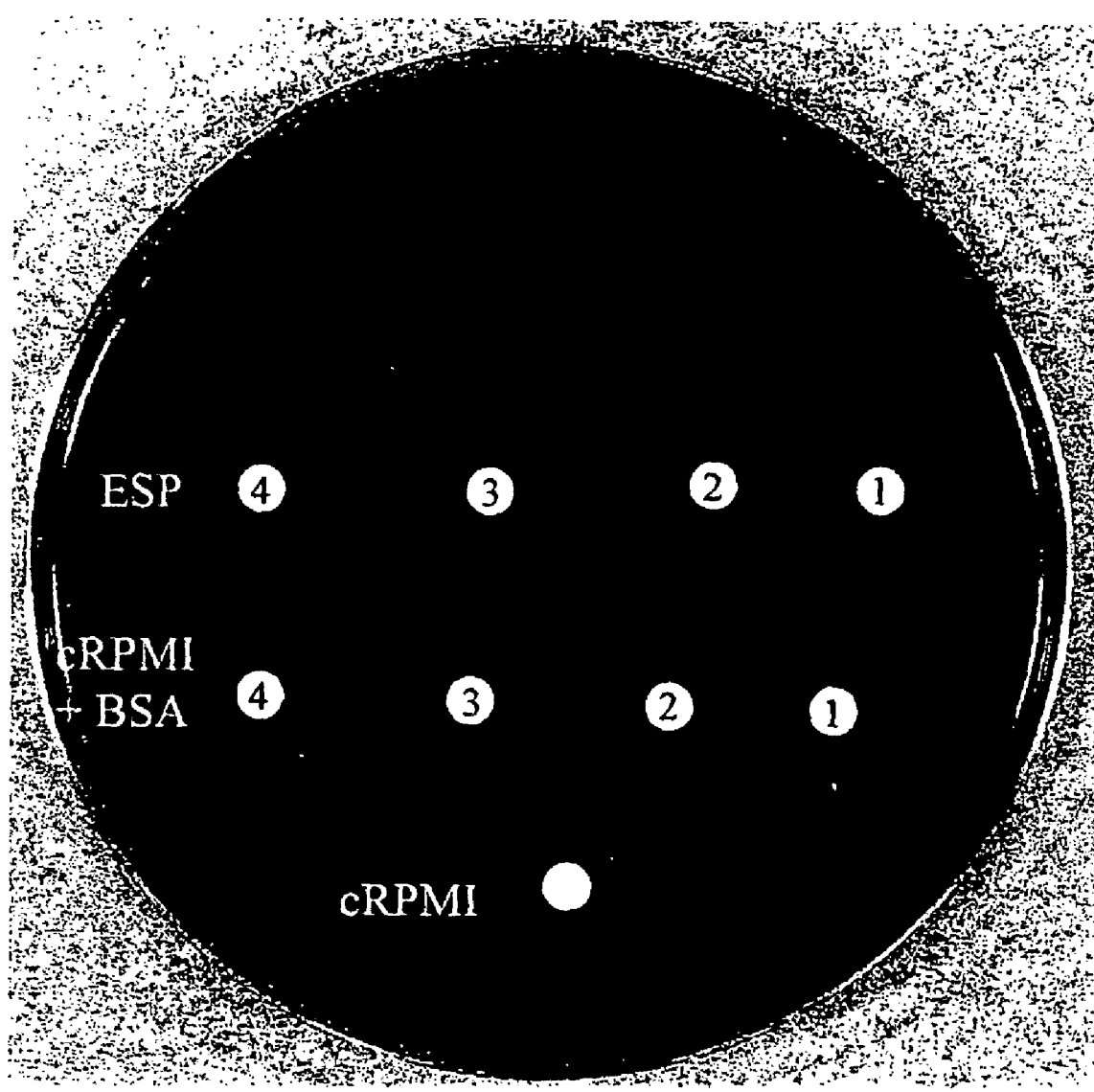
FIG. 1 shows that the inhibitory effect of ESP on the growth of *Campylobacter jejuni* was proportional to the ESP concentration in an agar diffusion assay. The disks were saturated with ESP at 4, 3, 2, and 1 mg ESP protein/ml corresponding to 80, 60, 40, and 20 µg total ESP protein/disk (top row), cRPMI containing BSA at concentration equivalent to the ESP (middle row), and cRPMI without dilution (bottom disk). There was no growth inhibition with cRPMI or cRPMI containing BSA.

Discovery of antibacterial activity in the ESP. The original ESP from *Trichuris suis* had a dose-dependent growth inhibitory effect on *Campylobacter jejuni* in the agar diffusion assay (FIG. 1). ESP concentrations of 80, 60, 40, and 20 µg total protein/disk had growth inhibition zones of 27, 25, 18, and 13 mm, respectively. Control cRPMI and cRPMI containing BSA at concentrations equivalent to ESP did not inhibit the growth of *Campylobacter jejuni*. The MICs of the antibacterial activity from the ESP on several *Campylobacter jejuni* and *Campylobacter coli* isolates were determined (Table 1). *Campylobacter jejuni* strains were consistently 2- to 4-fold more sensitive to ESP than *Campylobacter coli* isolates (Table 1). The MBC of ESP on *Campylobacter jejuni* 332Sf2 was equivalent to the MIC at 1:128.

To confirm that the antibacterial activity was not limited to Campylobacter spp., additional organisms were tested by the agar diffusion method (Table 2).

TABLE 2

Preliminary Inhibitory Spectrum of *Trichuris suis* ESP

| Test organism | Sensitivity[a] | |
|---|---|---|
| | 20 µg[b] | 2 µg[b] |
| *Escherichia coli* (Gram pos.) | + | − |
| *Pseudomonas aeruginosa* (Gram neg.) | − | − |
| *Staphylococcus aureus* (Gram pos.) | + | − |
| *Streptococcus pneumoniae* (Gram pos.) | − | − |
| *Enterococcus faecalis* (Gram pos.) | − | − |

Agar plates were inoculated from a suspension of test organisms containing $10^8$ cfu/ml.
[a]Susceptibility is refereed to by classifying organisms as resistant (−) or sensitive (+) to ESP as determined by the agar diffusion assay.
[b]Susceptibility discs were saturated with 20 µl of ESP at concentrations of 1 mg/protein/ml (20 µg total protein/disc) and 0.1 mg protein/ml (2 µg total protein/disc).

As shown in Table 2, two of the five quality control test organisms, one Gram-negative and one Gram-positive, were sensitive to ESP. *Escherichia coli* had a zone of growth inhibition 9 mm in diameter, whereas *Staphylococcus aureus* had a zone of 11 mm. Both organisms were sensitive only to the highest concentration of ESP tested (20 µg total protein/disk).

In a subsequent experiment, inocula of the susceptible quality control organisms were diluted to determine if sensitivity to ESP increased with decreasing numbers of organisms present. As shown in Table 3, the zones of growth inhibition were the same for all three inoculum sizes.

TABLE 3

Effect of Inoculum Size on ESP Sensitivity

| Test organism | Inoculum | | |
|---|---|---|---|
| | 1:10[a] | 1:100 | 1:1000 |
| *Escherichia coli* | 9[b] | 9 | 9 |
| *Staphylococcus aureus* | 11 | 11 | 11 |

[a]A suspension of organisms at $10^8$ cfu/ml was serially diluted to achieve $10^7$, $10^6$, and $10^5$ cfu/ml suspensions for inoculation of agar plates.
[b]Diameters of growth inhibition zones were measured in mm.

Stability of the antibacterial activity in the ESP and ultrafiltration of the antibacterial activity. As shown in Table 4, the antibacterial activity of the original *Trichuris suis* ESP was unaltered by heat treatment and repeated freeze-thawing. Furthermore, Table 4 shows that digesting the ESP with trypsin and pronase E did not abolish antibacterial activity. When the ESP was filtered through a 30K filter, the fractions above and below 30,000 MW contained antibacterial activity (Table 4). However, the antibacterial activity was lost in the 30K retentate after repeated dialysis. Sub-fractionation of the 30K filtrate on a 10,000 MW membrane also showed antibacterial activity in the retentate and filtrate.

TABLE 4

Physical and Chemical Properties of ESP antibacterial Activity

| Treatment | Activity[a] |
|---|---|
| Boiling | + |
| Freeze-thawing | + |
| Trypsin | + |

TABLE 4-continued

Physical and Chemical Properties of ESP antibacterial Activity

| Treatment | Activity[a] |
|---|---|
| Pronase E | + |
| 30K retentate | + |
| 30K filtrate | + |
| 10K retentate | + |
| 10K filtrate | + |
| 30K retentate dialyzed[b] | − |

[a]Antibacterial activity was measured qualitatively by the broth microdilution assay using *Campylobacter jejuni* as the test organism. Activity was classified as no growth (+) or growth (−).
[b]The 30K retentate was dialyzed and concentrated 5× in 100× volumes of RPMI-1640 on a YM30 membrane.

Figure 2A:
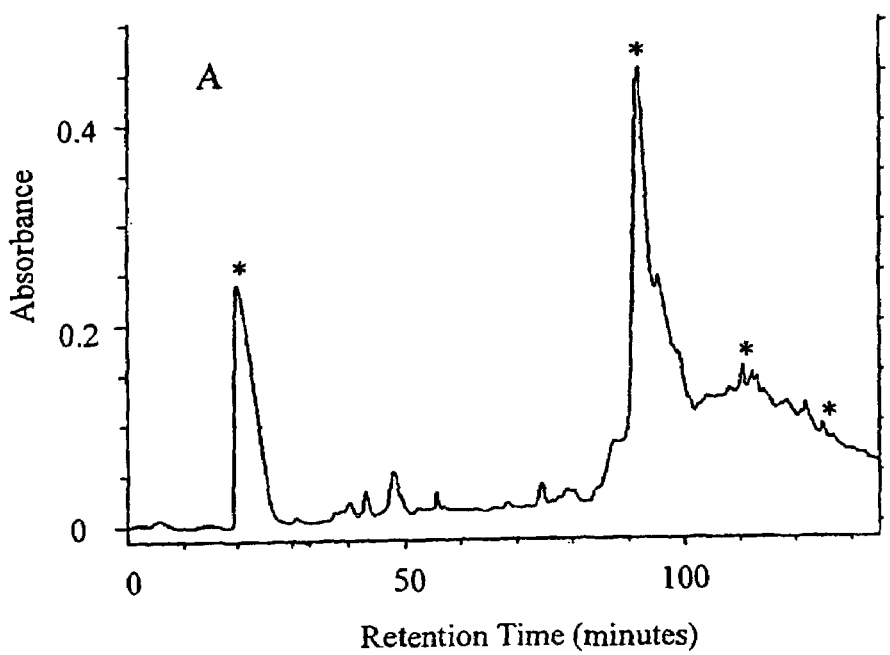
FIG. 2A shows that fractionation of the original *Trichuris suis* ESP on a C18 reverse phase HPLC column with a 5–80% ACN gradient in 0.1% TFA resulted in at least three fractions with antibacterial activity (identified by asterisks). The ESP sample was 100 µg in 0.02 ml and antibacterial activity was determined by the qualitative broth microdilution assay.
Figure 2B:
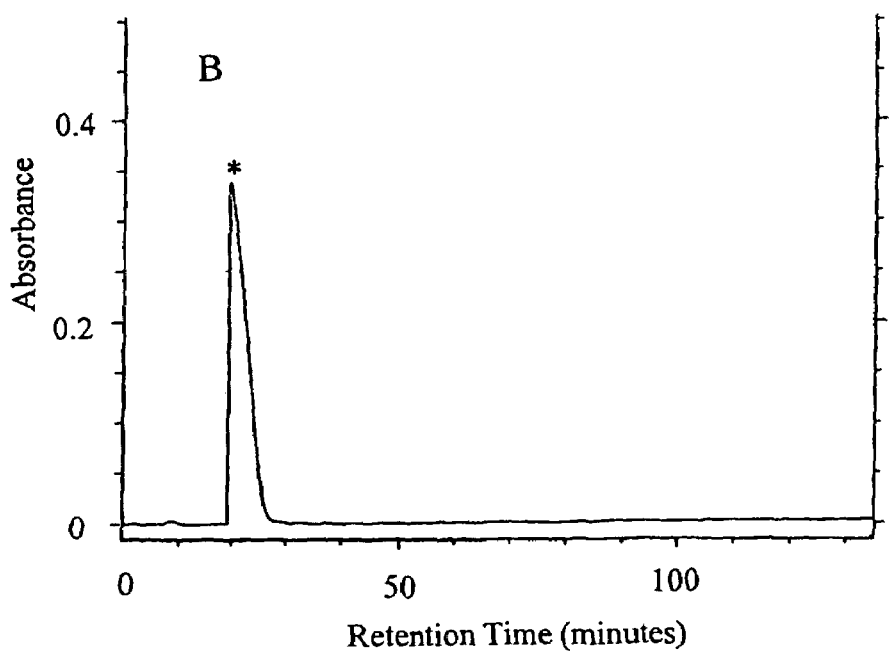
FIG. 2B shows that fractionation of the CAP standard on a C18 reverse phase HPLC column with a 5–80% ACN gradient in 0.1% TFA resulted in one fraction with antibacterial activity (identified by the asterisk). The CAP standard was 0.2 µg in 0.02 ml and antibacterial activity was determined by the qualitative broth microdilution assay.
Figure 3A:
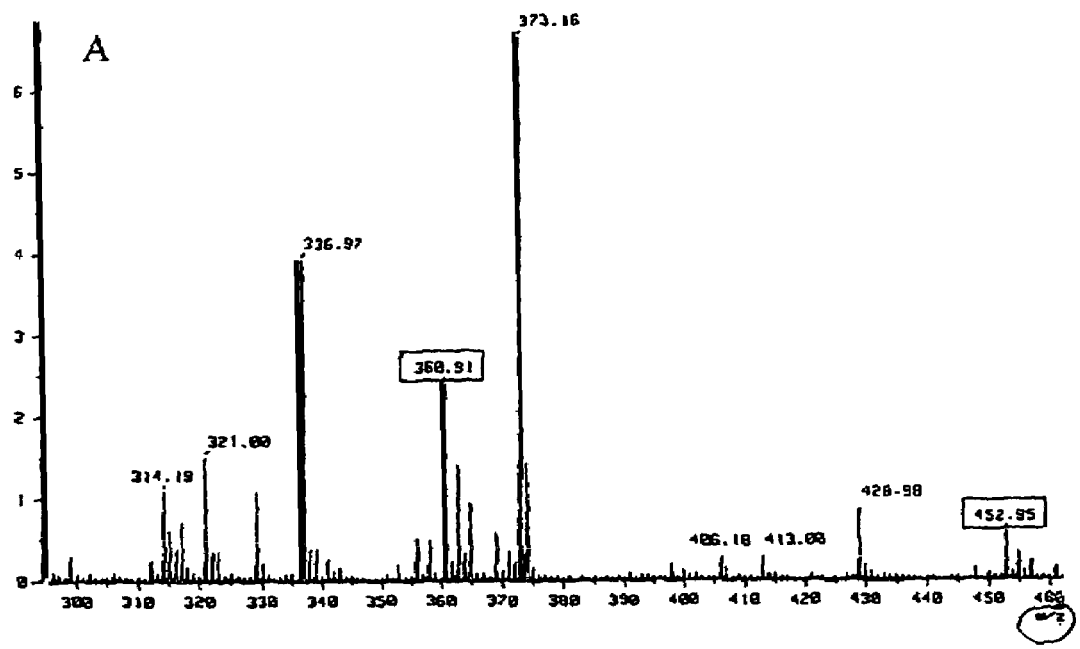
FIG. 3A shows MS of the ESP 20 minute fraction. The mass spectra was obtained by bombarding samples in a glycerol matrix with a beam of Xe atoms. The boxes indicate the characteristic patterns for CAP.
Figure 3B:
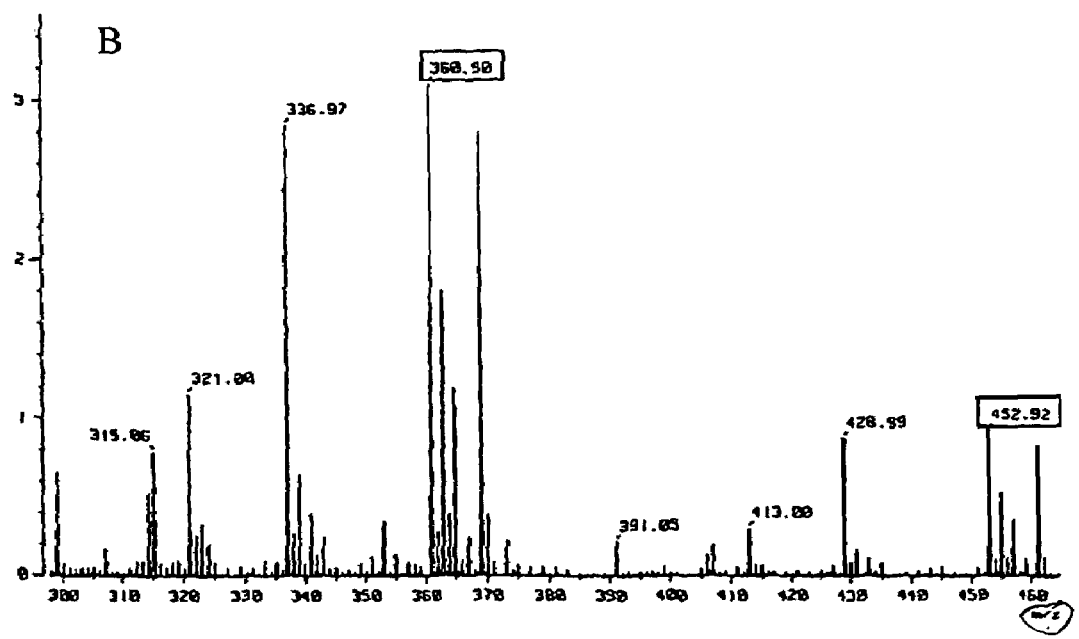
FIG. 3B shows MS of the CAP standard 20 minute fraction. The mass spectra was obtained by bombarding samples in a glycerol matrix with a beam of Xe atoms. The boxes indicate the characteristic patterns for CAP.

HPLC fractionation of the antibacterial activity in the ESP and mass spectrometry analysis of the antibacterial activity. Fractionation of the original ESP on a C18 reverse phase HPLC column showed that the antibacterial activity resided in several fractions with retention times ranging from about 20 minutes to over 100 minutes (FIG. 2A). Control HPLC experiments to test for residual antibiotics revealed that CAP co-eluted with the 20 minute ESP fraction (FIG. 2B). The other two antibiotics (PEN and STREP) and the antifungal agent (AMB) had no peaks matching those present in ESP (data not shown). By comparison to a CAP standard, mass spectrometry confirmed that the 20 minute ESP fraction contained CAP or a CAP-like molecule (FIGS. 3A and 3B). Comparison of peak heights in the ESP and CAP standard for HPLC and mass spectrometry experiments indicated that ESP contained less than 2 µg/ml residual CAP or a CAP-like molecule.

Consideration of CAP contamination in the ESP and removal of the CAP contamination from the ESP. The log PC of PEN indicated that it was too hydrophobic to be released back into the media following absorption by the whipworms (Table 5). In addition, PEN was inactivated by heat treatment (Table 6), which indicated that it was not be responsible for the heat-resistant activity in ESP. Although boiling did not inactivate STREP (Table 6), the log PC indicated that it was too hydrophilic to be absorbed by the nematode in any significant quantity (Table 5). The larger size of STREP would also contribute to its relative exclusion from absorption across the cuticle (Table 5).

TABLE 5

Physical Properties of Antibiotics

| Antibiotic | MW | log PC |
|---|---|---|
| Streptomycin sulfate | 728.70 | −9.53 (−) |
| Chloramphenicol | 323.13 | 0.92 (8.3×) |
| Penicillin G | 334.4 | 185 (71×) |

Molecular weight (MW) and n-octanol/water partition coefficient (log PC) were compiled from a drug database at Upjohn. Concentrating factors are in parentheses.

TABLE 6

Effect of Boiling On Antibiotics

| Antibiotic | Activity[a] |
|---|---|
| Streptomycin sulfate | + |
| Chloramphenicol | + |
| Penicillin G | − |

Antibiotics (133 concentration) were boiled for 10 minutes.
[a]Antibacterial activity was measured qualitatively by the broth microdilution assay using *Campylobacter jejuni* as the test organism.

Figure 4:
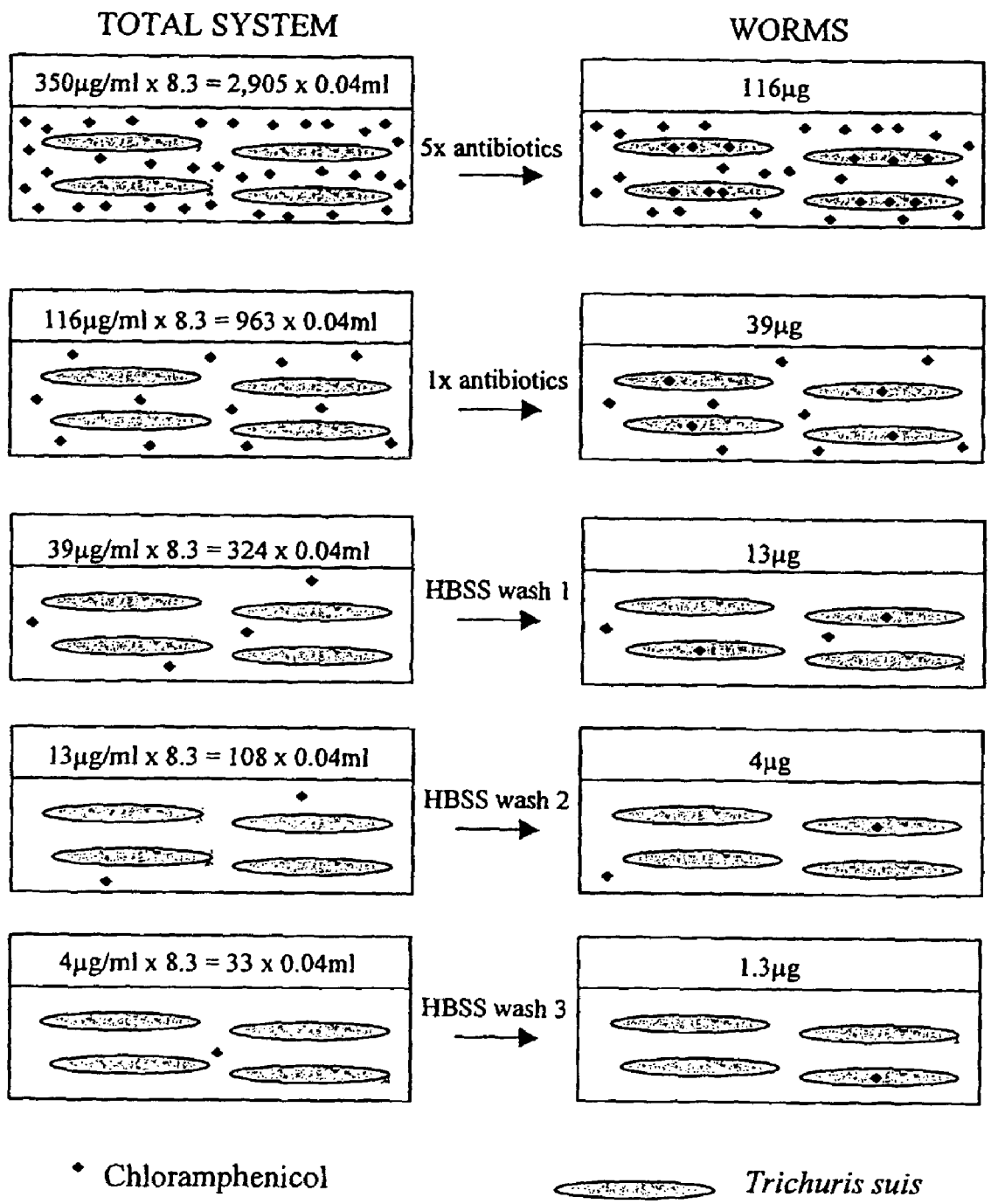
FIG. 4, shows the theoretical calculations estimating the residual CAP in the original ESP. Log PC values were used to predict the maximum amount of CAP absorbed by the aggregate whipworm volume (4% of the total system) and then released back into the medium using the worst-case scenario, i.e., that 100% was released.

However, the log PC of CAP predicted that it could be absorbed and then released by the whipworms, and further, CAP is not heat-inactivated (Tables 5 and 6). Therefore, an estimate of the maximum concentration of CAP in the trace levels of CAP remaining in the ESP after every step in the ESP production protocol was calculated (FIG. 4). The maximum concentration of CAP in the final ESP preparation after three washes with HBSS was estimated to be between about 1 to 2 µg CAP/ml. The estimate is consistent with the HPLC and mass spectrometry data. Also, it was experimentally determined that the MIC of CAP for *Campylobacter jejuni* was about 2 µg/ml. However, because the antibacterial activity was detectable in ESP diluted 1:100, the trace levels of CAP present in the final ESP was insufficient to account for the antibacterial activity in the ESP. A 1:100 dilution of ESP reduces the concentration of residual CAP to approximately 0.01 to 0.02 µg/ml, which is about 100× less than its MIC.

Although the protein yield of the CAP-free ESP was low, which was attributed to the limited nematode recovery from naturally infected pigs, antibacterial activity was clearly present. Despite the discrepancy in protein concentration, the antibacterial titers of the greater than 10,000 MW fraction of original ESP and CAP-free ESP were identical at 2560 AU/ml (Table 7). However, of particular interest was the observation that a high level of antibacterial activity (10,240 AU/ml) was in the 10K filtrate of the CAP-free ESP (Table 7). Comparison of the HPLC profiles from the 10K retentate and filtrate of the CAP-free ESP showed that the majority of the material was in the 10K filtrate, including the antibacterial activity (FIGS. 5A and 5B).

TABLE 7

Comparison of Antibacterial Titers in Original and CAP-Free ESP

|  | [protein][a] | 10K retentate[b] | 10K filtrate[b] |
| --- | --- | --- | --- |
| ESP | 3 | 2560 | 320[c] |
| CAP-free ESP | 0.1 | 2560 | 10,240 |

[a]Concentration of protein is mg/ml
[b]Activity in units/ml was calculated from the reciprocal of the MIC.
[c]Secondary filtrate because the original was not available.

Figure 6A:
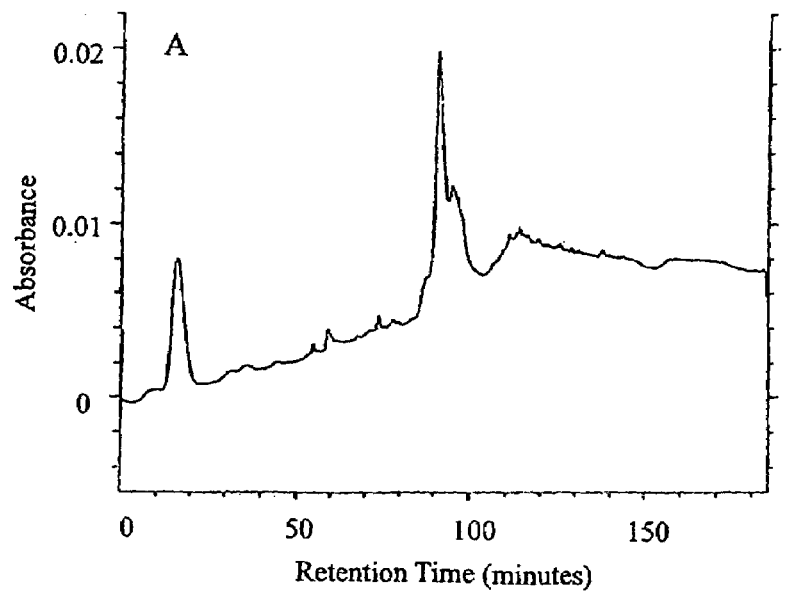
FIG. 6A shows that the HPLC profile for the original ESP 10K retentate fractionated on a reverse-phase C18 HPLC column with a 5–80% ACN gradient in 0.01% TFA. Sample was 10 μg in 0.02 ml.
Figure 6B:
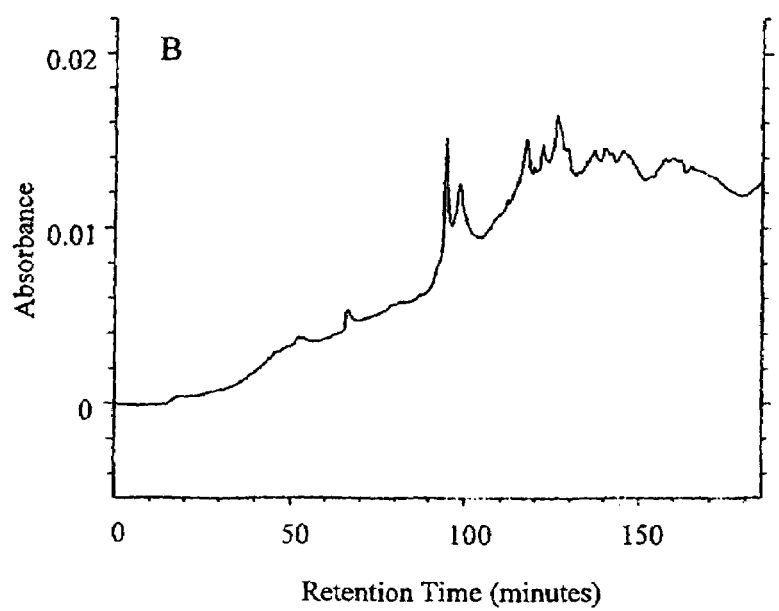
FIG. 6B shows that the HPLC profile for the CAP-free ESP 10K retentate fractionated on a reverse-phase C18 HPLC column with a 5–80% ACN gradient in 0.01% TFA. Sample was 10 μg in 0.02 ml.

The antibacterial activity in CAP-free ESP had characteristics identical to the original ESP in that it also was resistant to boiling, freezing-thawing, and inactivation by trypsin and pronase E (Table 8). Additionally, HPLC chromatographs of the 10K retentates from the original and CAP-free ESP were similar, with the exception of the missing 20 minute CAP peak (FIGS. 6A and 6B).

TABLE 8

Physical and Chemical properties of CAP-Free ESP Antibacterial Activity

| Treatment | Activity[a] |
| --- | --- |
| Boiling | + |
| Freeze-thawing | + |
| Trypsin | + |
| Pronase E | + |

[a]Antibacterial activity was measured qualitatively by the broth microdilution assay using *Campylobacter jejuni* as the test organism. Activity was classified as no growth (+) or growth (−).

DISCUSSION

As shown by this example, a potent antibacterial activity in ESP was isolated from adult *Trichuris suis*, a nematode which parasitizes the large intestine of swine. However, because ESP from an axenic culture of *Trichuris suis* cannot be prepared without initially high concentrations of antibiotics to prevent the overgrowth of fecal organisms associated externally and internally with the whipworms, it was imperative to exclude the antibiotics as the source for the antibacterial activity in the ESP. HPLC, mass spectrometry, the physicochemical properties of the antibiotics, and preparation of CAP-free ESP with antibacterial activity showed that the antibacterial activity in the ESP was native to *Trichuris suis* and not a consequence of the antibiotics used to prepare the ESP.

After detecting residual CAP in the ESP by HPLC and mass spectrometry, the extent to which PEN, STREP, and CAP would be carried over into the final ESP was estimated. Uptake of anthelminthic drugs by GI nematodes occurs primarily by absorption across the cuticle (Ho et al., Mol. Biochem. Para. 52: 1–13 (1992)). The cuticle is secreted by a single layer of cells that form the hypoclermis, and is composed of a dense collagen and collagen-like protein matrix containing negatively charged aqueous-filled pores (Ho et al., Mol. Biochem. Para. 41: 153–65 (1990); Fetterer and Rhoads, Vet. Para. 46: 103–11 (1993)). The rate-determining barrier for drug absorption is at the interface of the hydrophilic porous cuticle matrix and the underlying lipophilic hypodermis (Ho et al., J. Pharma. Sci. 83: 1052–9 (1994)). Absorption of anthelminthic compounds across the cuticle generally increases with lipophilicity of the agent and is also influenced by the: size of the drug. Molecules with $M_r$ greater than 350 KDa are absorbed less efficiently than smaller molecules (Ho et al., J. Pharma. Sci. 83: 1052–9 (1994)).

It is unlikely that residual PEN accounted for the antibacterial activity in the ESP because of its log PC and its sensitivity to inactivation by boiling (ESP retained its antibacterial activity after boiling). STREP was not a contaminant of the ESP because of its log PC and its size. The residual CAP that contaminated the original *Trichuris suis* ESP did not contribute significantly to the antibacterial activity in the ESP because the ESP antibacterial activity persisted in ESP in which the CAP had been diluted to about 100× less than its MIC, which is below the level at which CAP antibacterial activity is measurable, and because the antibacterial activity was present in CAP-free ESP.

It was considered highly unlikely that antibiotics could persist into the final ESP preparation, because the whipworms were washed extensively after antibiotic treatments. Nevertheless, low levels of residual CAP were detected by HPLC and confirmed by mass spectrometry. This observation underscores the importance of being cautious about routinely including antibiotics in the whipworm incubations. Therefore, it is preferable that CAP not be added to media used to grow *Trichuris suis* for preparation of ESP containing antibacterial activity.

The ESP antibacterial activity was effective against both Gram-negative and Gram-positive bacteria. Sensitivity to the ESP antibacterial activity was proportional to the concentration of ESP but was not influenced by the number of organisms in the inoculum. Because the MIC and MBC of the ESP antibacterial activity against *Campylobacter jejuni* were equal, the ESP antibacterial activity appears to be primarily bactericidal.

The presence of antibacterial activity in ESP which had been subjected to the harsh conditions of boiling, freezing-thawing, and exposure to trypsin and pronase E, indicated that the antibacterial activity resided in one or more stable molecules. The HPLC data of the ESP and CAP-free ESP showed that the antibacterial activity comprises at least three components, each with antibacterial activity. Although the antibacterial activity was resistant to proteases, particularly the highly nonspecific pronase E, it is still possible that the antibacterial activity resides in one or more short peptides. Data from the ultrafiltration experiments indicated that at least one of the components of the antibacterial activity comprises molecules which are about 10,000 MW or less in size.

Genes encoding antibacterial peptides have been identified in a variety of invertebrate species (Furukawa et al., Biochem. J. 15: 265–71 (1999); Park et al., Insect Biochem. Molec. Biol. 27: 711–20 (1997)). Alternatively, antibacterial activity is found in peptide fragments derived from larger proteins that have been degraded (Bellamy et al., Biochim. Biophys. Acta 1121: 130–6 (1992); Strub et al., Eur. J. Biochem. 229: 356–68 (1995)). It has been shown that *Trichuris suis* ESP proteins are degraded by a constituent zinc metalloprotease, which also undergoes auto degradation (Hill et al., Exper. Para. 77: 170–8 (1993)). It is possible that the antibacterial activity of the ESP is a degradation product of a larger *Trichuris suis* protein.

For example, the mechanism of many antibacterial peptides is pore-formation in bacterial cell membranes (Lockey and Ourth, Eur. J. Biochem. 236: 263–71 (1996); Maget-Dana and Peypoux, Toxicol. 87: 151–74 (1994); Leippe et al., Proc. Natl. Acad. Sci. USA 88: 7659–63 (1991); Leippe et al., Molec. Microbiol. 14: 895–904 (1994)). Therefore, a possible candidate for the source of the antibacterial activity of the trichuricin would be degradation products of the presumed *Trichuris suis* counterpart of the 50K pore-forming protein from *Trichuris trichuria* (TT5O) (Drake et al., Proc. Royal Soc. Lon. Ser. B: Biol. Sci. 257: 255–61 (1994);Drake et al., Proc. Royal Soc. Lon. Ser. B: Biol. Sci. 265: 1559–65 (1998)). TT50 produces ion channels in lipid bi-layers and it contains multiple cysteine residues forming disulfide bonds., which are a common feature of antibacterial peptides.

The trichuricin of the present invention is the first description of a novel antibacterial activity from *Trichuris suis*. Only one other parasitic nematode, *Ascaris suum*, has been shown to possess an antibacterial activity. However, the antibacterial activity was from the body fluid of *Ascaris suum* (Kato and Komatsu, J. Biol. Chem. 271: 30493–30498 (1996)) and not the ESP. The possibility that the antibacterial activity was a component of the ESP, which had accumulated in the body fluid of the *Ascaris suum*, is unlikely but cannot be ruled out.

EXAMPLE 2

This example shows the sequencing and synthesis of trichuricin.

The trichuricin is prepared and isolated from the ESP as in Example 1. The trichuricin is sequenced using peptide sequencing methods well known in the art. The sequence of the trichuricin antibacterial activities enables degenerate PCR primers to be made which can be used to identify the *Trichuris suis* genomic DNA encoding the antibacterial activities. The amino acid sequence allows synthetic trichuricin to be chemically synthesized using peptide synthesis technologies well known in the art.

EXAMPLE 3

This example shows the preparation of monoclonal antibodies that recognize the trichuricin.

The trichuricin is prepared and isolated from the ESP as in Example 1 or synthesized as in Example 2. Then the trichuricin is used to make monoclonal antibodies according to the methods in *Antibodies, A Laboratory Manual*. Harlow and Lane (Eds.), Cold Spring Harbor Laboratory Press, Cold Spring Harbor, N.Y. (1988), well known to those skilled in the art as a source for methods for making polyclonal and monoclonal antibodies. Because of the small size of the trichuricin (less than or equal to 100 amino acids), the trichuricin is preferably coupled to a carrier such as bovine serum albumin or keyhole limpet hemocyanin with a bifunctional reagent such as glutaraldehyde (amino to amino), m-Maleimidobenzoic acid-N-hydroxy-succinimide (MBS; amino to sulfhydryl), bisdiazo-benzidine (BDB; tyr to tyr), or carbodiimide (EDAC; amino to carboxyl) using methods well known in the art.

BALB/c mice are immunized with an initial injection of 1.0 μg of the trichuricin per mouse mixed 1:1 with Freund's complete adjuvant. After two weeks, a booster injection of 1.0 μg of the trichuricin is injected into each mouse intravenously without adjuvant. Three days after the booster injection the mouse serum is checked for antibodies to the trichuricin. If positive, a fusion is performed with a mouse myeloma cell line. Mid log phase myeloma cells are harvested on the day of fusion, checked for viability, and separated from the culture medium by low-speed centrifugation. Then the cells are resuspended in serum-free Dulbecco's Modified Eagle's medium (DMEM).

The spleens are removed from the immunized mice and washed three times with serum-free DMEM and placed in a sterile Petri dish containing 20 ml of DMEM containing 20% fetal bovine serum, 1 mM pyruvate, 100 units penicillin, and 100 units streptomycin. The cells are released by perfusion with a 23-gauge needle. Afterwards, the cells are pelleted by low-speed centrifugation and the cell pellet is resuspended in 5 ml 0.17 M ammonium chloride and placed on ice for several minutes. Then 5 ml of 20% bovine fetal serum is added and the cells pelleted by low-speed centrifugation. Afterwards, the cells are resuspended in 10 ml DMEM and mixed with myeloma cells to give a ratio of 3:1. The cell mixture is pelleted by low-speed centrifugation, the supernatant fraction removed, and the pellet allowed to stand for 5 minutes. Next, over a period of 1 minute, 1 ml of 50% polyethylene glycol (PEG) in 0.01 M HEPES pH 8.1 at 37° C. is added. After 1 minute incubation at 37° C., 1 ml of DMEM is added for a period of another 1 minute, then a third addition of DMEM is added for a further period of 1 minute. Finally, 10 ml of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 μM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the trichuricin. One hundred μl of supernatant from each well is added to a corresponding well on a screening plate and incubated for 1 hour at room temperature. After incubation, each well is washed three times with water and 100 μl of a horseradish peroxidase conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 μl of 1 M HCl is added to stop the reaction and the absorbance of the wells is measured at 490 nm. Cultures that have an absorbance greater than the control wells are removed to 2 cm² culture dishes, with the addition of normal mouse spleen cells in HAT medium. After a further three days, the cultures are re-screened as above and those that are positive are cloned by limiting dilution. The cells in each 2 cm² culture are counted and the cell concentration adjusted to $1\times10^5$ cells/ml. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 cm² cultures and provided with normal mouse spleen cells. This cloning procedure is repeated until stable antibody producing hybridomas are obtained. Then the identified stable hybridomas are progressively expanded to larger culture dishes to provide stocks of the cells.

Production of ascites fluid is performed by injecting 0.5 ml of pristane intraperitoneally into female mice to prime the mice for ascites production. After 10 to 60 days, $4.5\times10^6$ cells are injected intraperitoneally into each mouse and ascites fluid is harvested between 7 and 14 days later.

Hybridomas that successfully produce monoclonal antibodies against trichuricin are expanded as above, and used to make monoclonal antibodies for purifying the trichuricin from ESP and for identifying DNA library clones which express the trichuricin.

EXAMPLE 4

This example shows the preparation of polyclonal antibodies that recognize the trichuricin.

The trichuricin is prepared and isolated from the ESP as in Example 1 or synthesized as in Example 2. Then the trichuricin is used to make polyclonal antibodies according to the methods in *Antibodies, A Laboratory Manual*. Harlow and Lane (Eds.), Cold Spring Harbor Laboratory Press, Cold Spring Harbor, N.Y. (1988), well known to those skilled in the art as a source for methods for making polyclonal and monoclonal antibodies. Because of the small size of the trichuricin (less than or equal to 100 amino acids), the trichuricin is preferably coupled to a carrier such as bovine serum albumin or keyhole limpet hemocyanin with a bifunctional reagent such as glutaraldehyde (amino to amino), m-Maleimidobenzoic acid-N-hydroxy-succinimide (MBS; amino to sulfhydryl), bisdiazo-benzidine (BDB; tyr to tyr), or carbodiimide (EDAC; amino to carboxyl) using methods well known in the art.

Rabbits are immunized preferably by the Vaitukaitis protocol: multiple intradermal immunizations at once. The upper back of the rabbit is shaved prior to immunization. About 1 mg of peptide is used per immunization (3–5 intradermal sites at each immunization), and the rabbits re-immunized at 2–6 week intervals. For the initial immunization, the immunogen (peptide-carrier conjugate) is mixed with an equal volume of complete Freund's adjuvant. For boosts, the immunogen is mixed with incomplete Freund's adjuvant. After the initial immunization and 2–3 boosts, the rabbits are bled 3–4 weeks later, and the antibodies tested by immunoprecipitation of $^{125}$I-labeled peptide.

The polyclonal antibodies are used for purifying the trichuricin from ESP and for identifying DNA library clones which express the trichuricin.

EXAMPLE 5

This example shows the preparation of a DNA library that expresses the trichuricin. The methods for making and screening DNA expression libraries are well known to those skilled in the art and are described in *Molecular Cloning: A Laboratory Manual, Second Edition*. Sambrook et al. (Eds.), Cold Spring Harbor Laboratory Press, Cold Spring Harbor, N.Y. (1989). The monoclonal antibodies made as in Example 3 or polyclonal antibodies made as in Example 4 are used to screen the library for clones that express the trichuricin.

Clones encoding the trichuricin are used to provide DNA encoding the trichuricin. The DNA, when under the control of an inducible promoter, is used to express the trichuricin in an expression vector in *E. coli*. The expressed trichuricin is purified for use.

Alternatively, DNA encoding the trichuricin is obtained by purifying the trichuricin by HPLC as described in Example 1 and sequencing the trichuricin. Degenerate PCR primers are made which are then used in a PCR reaction containing *Trichuris suis* genomic DNA to PCR amplify a DNA product containing nucleotide sequences encoding the trichuricin. The amplified PCR product is used as a probe to identify *Trichuris suis* genomic DNA and cDNA containing the nucleotide sequences encoding the trichuricin. The DNA encoding the trichuricin is isolated and cloned into a plasmid with a promoter for expressing the trichuricin. The plasmid encoding the trichuricin is transformed into a suitable organism for expression of the trichuricin.

EXAMPLE 6

The antibacterial activity of the trichuricin of the present invention is purified from the ESP of *Trichuris suis* by HPLC as shown in Example 1. The HPLC fractions which are identified (as shown in FIGS. 2 and 5) as containing the antibacterial activity are purified and used to produce compositions, mixtures, and solutions which contain the trichuricin of the present invention. Alternatively, the trichuricin is produced from an expression vector or chemically synthesized.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for producing one or more HPLC fractions having an antibacterial activity from an excretory-secretory product of *Trichuris suis* which inhibits the growth of *Campylobacter jejuni* as an assay strain in a growth medium, wherein the antibacterial activity is resistant to boiling, freeze-thawing, trypsin and pronase E, which comprises:
   (a) culturing the *Trichuris suis* in vitro in a serum-free medium; and
   (b) separating the excretory-secretory product with the antibacterial activity from the medium by HPLC; and
   (c) selecting one or more HPLC fractions which comprise at least one molecule having the antibacterial activity which has a molecular weight of 10,000 or less.

2. The method of claim 1 wherein the one or more HPLC fractions having the antibacterial activity inhibit at least one species of Gram positive or Gram negative bacteria by at least 50%.

3. The method of claim 2 wherein the one or more HPLC fractions having the antibacterial activity inhibit a bacteria selected from the group consisting of *Campylobacter jejuni, Campylobacter coli, Escherichia coli,* and *Staphylococcus aureus*.

4. The method of claim 1 wherein the HPLC uses a reverse phase C18 column and a gradient to separate an eluate having the antibacterial activity.

5. The method of claim 4 wherein the gradient is a 5–80% acetonitrile gradient in 0.1% trifluoroacetic acid.

6. The method of claim 5 wherein the eluate having the antibacterial activity is eluted from the HPLC column at between about 1 to 10 minutes.

7. The method of claim 5 wherein the eluate having the antibacterial activity is eluted from the HPLC column at between about 40 to 50 minutes.

8. The method of claim 5 wherein the eluate having the antibacterial activity is eluted from the HPLC column at between about 60 to 70 minutes.

* * * * *

UNITED STATES PATENT AND TRADEMARK OFFICE
CERTIFICATE OF CORRECTION

PATENT NO. : 7,052,874 B2 Page 1 of 1
APPLICATION NO. : 10/415166
DATED : May 30, 2006
INVENTOR(S) : Linda S. Mansfield and Sheila Abner It is certified that error appears in the above-identified patent and that said Letters Patent is hereby corrected as shown below:

Column 3, line 37, "perenteral" should be --parenteral--.

Column 7, line 11, "perenteral" should be --parenteral--.

Column 11, line 61, "could persist if" should be --could persist--.

Column 14, line 38, "that it was not be" should be --that it was not--.

Column 14, line 64, "Antibiotics (133 concentration)" should be --Antibiotics (1x concentration)--.

Signed and Sealed this

Eleventh Day of December, 2007

JON W. DUDAS
*Director of the United States Patent and Trademark Office*